United States Patent [19]

Henrick

[11] 3,969,385

[45] July 13, 1976

[54] ETHYL 10-METHOXY-3,7,11-TRIMETHYL-DODECA-2,4-DIENOATE

[75] Inventor: Clive A. Henrick, Palo Alto, Calif.

[73] Assignee: Zoecon Corporation, Palo Alto, Calif.

[22] Filed: Dec. 6, 1974

[21] Appl. No.: 530,122

[52] U.S. Cl. .................. 260/410.9 R; 424/31 R
[51] Int. Cl.² ............................................ C11C 3/02
[58] Field of Search ......................... 260/410.9 R

[56] References Cited
UNITED STATES PATENTS

| | | | |
|---|---|---|---|
| 3,755,411 | 8/1973 | Henrick | 260/410.9 R |
| 3,801,608 | 4/1974 | Henrick | 260/410.9 R |
| 3,801,611 | 4/1974 | Henrick | 260/410.9 R |

Primary Examiner—Winston A. Douglas
Assistant Examiner—John F. Niebling
Attorney, Agent, or Firm—Donald W. Erickson

[57] ABSTRACT

Ethyl 10-methoxy-3,7,11-trimethyldodeca-2,4-dienoate is useful for the control of insects, in particular, Lepidopteran such as Pyralidae, Noctuidae, and Gelechiidae.

3 Claims, No Drawings

ETHYL 10-METHOXY-3,7,11-TRIMETHYLDODECA-2,4-DIENOATE

This invention relates to a novel compound and its use for the control of insects.

U.S. Pat. No. 3,755,411 teaches the use of ethyl 11-methoxy-3,7,11-trimethyldodeca-2,4-dienoate for the control of insects.

It has now been found that improved control of insects and particularly of Lepidopteran insects can be obtained by the use of ethyl 10-methoxy-3,7,11-trimethyldodeca-2,4-dienoate of the formula:

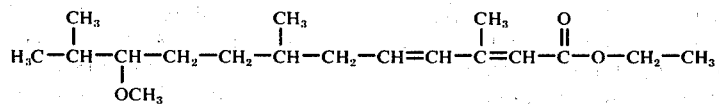

The utility of this compound as an insect control agent is believed to be attributable to its juvenile hormone activity. It is preferably applied to the immature insect, namely-during the embryo, larva or pupa stage in view of its effect on metamorphosis, causing abnormal development leading to death or inability to reproduce. This compound is an effective control agent for Hemipteran such as Lygaeidae, Miridae and Pyrrhocoridae; Coleopteran such as Tenebrionidae, Crysomlidae and Dermestidae and other insects and particularly for Lepidopteran such as Pyralidae, Noctuidae and Gelechiidae. The compound can be applied at low dosage levels of the order of 0.001 $\mu$g to 25 $\mu$g per insect. Suitable carrier substances include liquid or solid carriers, such as water, acetone, xylene, mineral or vegetable oils, talc, vermiculite, natural and synthetic resins and silica. Treatment of insects in accordance with the present invention is accomplished by spraying, dusting or exposing the insects to the vapor of ethyl 10-ethoxy-3,7,11-trimethyldodeca-2,4-dienoate. Generally, a concentration of less than 25% of the active compound is employed. The formulations can include insect attractants, emulsifying agents or wetting agents to assist in the application and effectiveness of the active ingredient.

The presence of the olefinic bonds at positions C-2 and C-4 gives rise to four isomers, each of which is embraced by the present invention. The conditions of reaction can be selected so as to favor the formation of one isomer such as the trans-2, trans-4 isomer over the formation of other isomers. The selection of appropriate conditions will be apparent to one skilled in the art. The trans-2, trans-4 and cis-2, trans-4 isomers are conveniently separated by preparative thin layer chromatography. In the application of the compounds, there is generally employed a mixture of the trans-4, trans-2 and trans-4, cis-2 isomers.

Ethyl 10-methoxy-3,7,11-trimethyldodeca-2,4-dienoate can be conveniently prepared by reacting 6-methoxy-3,7-dimethyl-1-octanol with triethyl-3-methyl-4-phosphonocrotonate which is prepared using the methods as described by Patlenden and Weedon, J. Chem. Soc. (C), 1984 and 1997 (1968), Stilz and Pommer, U.S. Pat. Nos. 3,163,669 and 3,177,226, and Corey et al., Tetrahedron Letters No. 2, 1821 (1971).

The following examples are provided to illustrate the practice of the present invention.

EXAMPLE 1 a. To 15.5 g. of citronellal is added 120 ml. of absolute methanol containing 0.05% sulfuric acid. The mixture is allowed to stand at room temperature for 3 hours and then aqueous sodium carbonate is added until the solution is basic phenolphthalein. Most of the methanol is removed under reduced pressure and the residue is shaken with a water-immiscible solvent such as hexane. The organic phase is separated and the solvent is removed under reduced pressure to yield the dimethyl acetal of citronellal.

b. To the dimethyl acetal of citronellal prepared in (a) is added 50 ml. of a 1M solution of diborane in tetrahydrofuran while the temperature of the reaction mixture is maintained at $-10°$ to $0°$ .C. The reaction mixture is stirred at 0°C for 45 minutes and then at 20°C for 30 minutes. To this mixture is added 12.0 g. sodium hydroxide, as a 50% aqueous solution. Hydrogen peroxide (as a 30% aqueous solution) is added dropwise until residual peroxide is present. Heat evolved during this addition is dissipated by permitting the solvent to distill under reflux. The reaction mixture is shaken with hexane, the hexane layer is separated and washed in turn with 5% aqueous sodium sulfite solution and saturated brine. Solvent is removed from the solution under reduced pressure and the residue is distilled to yield the dimethyl acetal of 3,7-dimethyl-6-hydroxyoctan-1-al.

c. To the dimethyl acetal prepared in (b) above is added 25 ml. of 1,2-dimethoxyethane and 3.9 g. potassium. The reaction mixture is stirred vigorously with gentle warming, followed by refluxing until all the potassium metal dissolves. Dimethylsulfate (12.6 g.) is added to the refluxing solution, followed after 2 hours by addition of 100 ml. of 2N aqueous sodium hydroxide. The resultant 3,7-dimethyl-6-methoxyoctan-1-al dimethyl acetal is isolated by shaking the reaction mixture with hexane, separating the hexane phase, washing it with saturated brine and removing the solvent under reduced pressure. To the acetal prepared in (c) is added 200 ml. of tetrahydrofuran and 40 ml. of 1N sulfuric acid. The solution is stirred for 10 hours at room temperature then most of the tetrahydrofuran is removed by distillation under reduced pressure. The residue is made basic with saturated aqueous sodium bicarbonate and extracted with hexane. The hexane layer is separated, washed with saturated brine and distilled to yield 3,7-dimethyl-6-methoxyoctan-1-al.

EXAMPLE 2

To a mixture of 5.88 g. of 6-methoxy-3,7-dimethyloctan-1-al, 9.9 g. of 80% pure triethyl 3-methyl-4-phosphonocrotonate, and 40 ml. dimethyl formamide, under nitrogen, is slowly added 1.32 g. of powdered sodium hydroxide. The mixture is stirred overnight at room temperature and then is worked up by adding 200 ml. of water and 200 ml. of ether followed by acidification to pH2 and separation of the organic layer. The organic layer is washed twice with 100 ml. water and dried over sodium sulfate. The solvent is removed by rotary evaporation and the product purified by distillation to yield 6.51 g. of ethyl 10 methoxy-3,7,11-trimethyldodeca-2,4-dienoate, 61% trans-2, trans-4, 39% cis-2, trans-4, boiling point 115°–117°C at 0.06 mm Hg (short path distillation).

The biological activity of ethyl 10-methoxy-3,7,11-trimethyldodeca-2,4-dienoate is illustrated by the following examples. Table 1 summarizes the activity of this compound as compared using the same biological testing procedures to the prior art compound ethyl 11-methoxy-3,7,11-trimethyldodeca-2,4-dienoate.

EXAMPLE 3

Greater Wax Moth (*Galleria mellonella*) pupae less than 24-hours old were collected after mature larvae from a mass colony were allowed to pupate in glass tubes treated with Siliclad solution (modification of a technique described by De Wilde et al., 1968) and then freed of the cocoon with a dilute Chlorox solution. Starvation of mature larvae was employed to produce highly synchronous pupation. One microliter of acetone solution containing 100, 10, 1, 0.1, 0.01, or 0.001 $\mu$g of compound was applied to the mouth-parts of each test pupa. In each test series, the control pupae were treated only with 1 microliter of acetone. Treated pupae were allowed to develop for 10 days at 31° and then scored for both retention of pupal characters and adult emergence. For the retention of pupal characters, the following scoring system was used: 0=normal adult; 1=minor pupal rudimentary mandibles only; 2=as in 1, but also pupal cuticle patches at the base of the proboscis; 3=extensive pupal cuticle formation at base of proboscis, slight pupal characters in intersegmental membranes in legs; 4=proboscis entirely pupal, larger than normal, legs with extensive pupal zones; 5=merging pupal bands on legs, specimen with only a few adult setae, essentially "a second pupa."

The graded-response score was calculated as a percentage of the maximum attainable ($n\times5$) and plotted against the dose on semilogarithmic paper. The $ID_{50}$ dose is taken from the intersection of this plotted line with the 50% effect level. The $ID_{50}$ for ethyl 10-methoxy-3,7,11-trimethyldodeca-2,4-dienoate is 0.0030 $\mu$g per pupa and the $ID_{50}$ for ethyl 11-methoxy-3,7,11-trimethyldodeca-2,4-dienoate is 0.180 $\mu$g per pupa.

EXAMPLE 4

*Philosamia cynthia* eggs less than 24-hours old were removed from the colony and placed on black electrical tape, 15 eggs per tape. One microliter of acetone solution containing 1, 0.1, 0.01, 0.001, 0.0001, or 0.001 $\mu$g of compound was applied to each egg. The control eggs were treated only with acetone. The eggs were kept at 28°C for 10 days at which time the number of eggs hatched was observed and plotted against the dosed on semilogarithmic paper. The $ID_{50}$ dose is taken from the intersection of this plotted line with the 50% hatch prevented line. The $ID_{50}$ for ethyl 10-methoxy-3,7,11-trimethyldodeca-2,4-dienoate was 0.000032 $\mu$g per egg; the $ID_{50}$ for ethyl 11-methoxy-3,7,11-trimethyldodeca-2,4-dienoate was 0.00077 $\mu$g per egg.

EXAMPLE 5

Tobacco budworm (*Heliothis virescens*) larvae were reared in mass culture on a modified Van der Zandt artificial diet based on agar, lima beans, split peas, torula yeast plus vitamins, minerals and bacteriostatic additives. Compounds to be tested were mixed as acetone solutions with this diet while it was still warm and not yet solidified (7.5 ml. of medium in 15 ml. tubes). Unfed first instar larvae were collected from the mass rearing and distributed in the glass tubes (one larva per tube, 15 tubes per dose level). The tubes with larvae were then capped with a firm cotton plug and placed on racks in a culture room at 25° and 16 hr photophase (low intensity fluorescent light). The normal interval until pupation under these conditions was ca. 16 days.

Individual specimens were preserved in ethanol within a few days after pupation and stored until the entire series was thus preserved. The test results were then evaluated with the following scoring system: 0=normal pupa; 1=pupa of normal shape and appearance except for very minor abnormalities such as minute rudiments of larval mouthparts, larval tubercles, etc. The ultimate viability of these pupa was not investigated; 2=unviable intermediates between larvae and pupae ranging from almost perfect supernumerary larval instars (frequently with some pupal cuticle on the antennae only) to pupae with pronounced prolegs, patches of larval cuticle, etc. These intermediates invariably showed a delayed development. The results were added and expressed as a percentage of the possible total. $ID_{50}$ doses were determined by interpolation on semilogarithmic paper. Dead larvae were generally excluded from the score, unless death was obviously a consequence of morphogenetic abnormalities and the specimens could be scored as above. The $ID_{50}$ for ethyl 10-methoxy-3,7,11-trimethyldodeca-2,4-dienoate is 0.024 parts per million and for ethyl 11-methoxy-3,7,11-trimethyl-2,4-dodecadienoate is 0.340 parts per million.

TABLE 1

| Compound | Isomer | Ratio | Summary of Biological Testing Galleria | Cynthia | Heliothis |
|---|---|---|---|---|---|
| | | | $ID_{50}\mu$g/pupa | $ID_{50}\mu$g/pupa | $ID_{50}$ ppm |
| ethyl 10-methoxy-3,7,11-trimethyl-dodeca-2,4-dienoate | 61% | trans-2, trans-4 | | | |
| | 39% | cis-2, trans-4 | 0.0030 | 0.000032 | 0.024 |
| ethyl 11-methoxy-3,7,11-trimethyl-dodeca-2,4-dienoate | 60% | trans-2, trans-4 | | | |
| | 40% | cis-2, trans-4 | 0.180 | 0.00077 | 0.340 |

I claim as my invention:

1. The compound ethyl 10-methoxy-3,7,11-trimethyldodeca-2,4-dienoate.
2. A mixture of the trans-2, trans-4 and cis-2, trans-4 isomers of the compound of claim 1.
3. The trans-2, trans-4 isomer of the compound of claim 1.